(12) United States Patent
Barth et al.

(10) Patent No.: US 7,345,059 B2
(45) Date of Patent: Mar. 18, 2008

(54) DIPHENYLPYRIDINE DERIVATIVES, PREPARATION AND THERAPEUTIC APPLICATION THEREOF

(75) Inventors: Francis Barth, Montpellier (FR); Laurent Hortala, Jacou (FR); Murielle Rinaldi-Carmona, Saint Georges d'Orques (FR)

(73) Assignee: Sanofi-Aventis, Paris (FR)

( * ) Notice: Subject to any disclaimer, the term of this patent is extended or adjusted under 35 U.S.C. 154(b) by 217 days.

(21) Appl. No.: 11/316,510

(22) Filed: Dec. 22, 2005

(65) Prior Publication Data

US 2006/0189664 A1    Aug. 24, 2006

Related U.S. Application Data

(63) Continuation of application No. PCT/FR2004/001581, filed on Jun. 24, 2004.

(30) Foreign Application Priority Data

Jun. 26, 2003   (FR) .................... 03 07757

(51) Int. Cl.
   *A61K 31/445*   (2006.01)
   *C07D 213/02*   (2006.01)
   *C07D 405/02*   (2006.01)

(52) U.S. Cl. .............. 514/318; 546/184; 546/192; 546/193; 546/268.1; 546/281.7; 546/283.4; 514/315

(58) Field of Classification Search .......... 546/184, 546/192, 193, 268.1, 281.7, 283.4; 514/315, 514/348
   See application file for complete search history.

(56) References Cited

FOREIGN PATENT DOCUMENTS

| FR | 2816938 | 5/2002 |
| WO | WO 97/19063 | 5/1997 |
| WO | WO 03/082191 | 10/2003 |
| WO | WO 03/084930 | 10/2003 |
| WO | WO 03/084943 | 10/2003 |

OTHER PUBLICATIONS

Roger G. Pertwee, Cannabinoid receptor ligands: clinical and neuropharmacological considerations, relevant to future drug discovery and development, Exp. Opin Invest. Drugs (2000, pp. 1553-1571, vol. 9 (7).

*Primary Examiner*—Golam M. M. Shameem
(74) *Attorney, Agent, or Firm*—Balaram Gupta

(57) ABSTRACT

The invention relates to 5,6-diphenylpyridine-3-carboxamide derivatives of general formula (I):

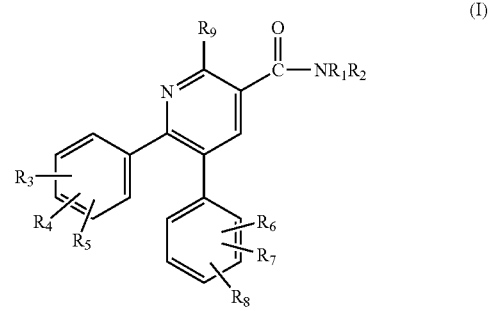

where:
   $R_1$ represents hydrogen or a ($C_1$-$C_4$)alkyl;
   $R_2$ represents:
      a monoazo saturated heterocycle of 5 to 7 atoms, the nitrogen atom being substituted with a ($C_1$-$C_4$)alkanoyl;
      $NR_{10}R_{11}$;
      a nonaromatic ($C_3$-$C_{10}$) carbocycle more than tri-substituted with ($C_1$-$C_4$)alkyl;
      a nonaromatic ($C_{11}$-$C_{12}$) carbocycle unsubstituted or mono- or polysubstituted with ($C_1$-$C_4$)alkyl;
      a monooxygenated saturated heterocycle with 5 to 7 atoms, more than tri-substituted with ($C_1$-$C_4$)alkyl;
   or $R_1$ and $R_2$, together with the nitrogen atom to which the above are bonded, form a 4-disubstituted piperidin-1-yl group;
the salts, solvates and hydrates thereof. The invention further relates to a method for production and therapeutic application thereof.

9 Claims, No Drawings

DIPHENYLPYRIDINE DERIVATIVES, PREPARATION AND THERAPEUTIC APPLICATION THEREOF

CROSS REFERENCE TO RELATED APPLICATIONS

This application is a continuation of International application No. PCT/FR2004/001581, filed Jun. 24, 2004, which is incorporated herein by reference in its entirety; which claims the benefit of priority of French Patent Application No. 03/07757, filed Jun. 26, 2003.

BACKGROUND OF THE INVENTION

1. Field of the Invention

The present invention relates to 5,6-diphenyl-pyridine-3-carboxamide derivatives, to the preparation thereof and to the application thereof in therapeutics.

2. Description of the Art 5,6-Diphenyl-2-pyridine derivatives are described in the international patent application published under No. WO 92/02513. These compounds are presented as having antithrombotic, vasodilating and anti-inflammatory activity.

Inverse agonist or antagonist 2,3-diphenylpyridine derivatives of cannabinoid $CB_1$ receptors are described in international patent application WO 2003/082191.

Novel 5,6-diphenyl-3-pyridinecarboxamide derivatives which possess cannabinoid $CB_1$ receptor antagonist properties have now been found.

SUMMARY OF THE INVENTION

Thus, a subject of the present invention is a compound of formula:

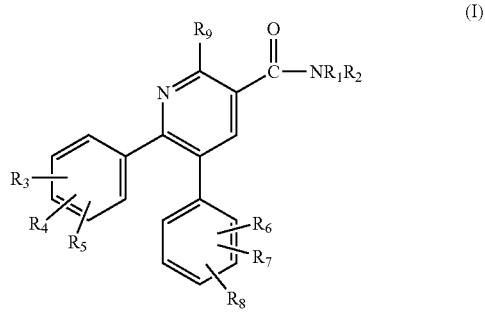

(I)

in which:
$R_1$ represents hydrogen or a $(C_1-C_4)$alkyl;
$R_2$ represents:
  a saturated mononitrogenous heterocyclic radical containing from 5 to 7 atoms, the nitrogen atom being substituted with a $(C_1-C_4)$alkanoyl group;
  a group $NR_{10}R_{11}$;
  a nonaromatic $C_3-C_{10}$ carbocyclic radical which is substituted more than three times with a $(C_1-C_4)$alkyl group;
  a nonaromatic $C_{11}-C_{12}$ carbocyclic radical which is unsubstituted or substituted one or more times with a $(C_1-C_4)$alkyl group;
  a saturated monooxygenated heterocyclic radical containing from 5 to 7 atoms, which is substituted more than 3 times with a $(C_1-C_4)$alkyl group;
  or $R_1$ and $R_2$, together with the nitrogen atom to which they are attached, constitute a piperidin-1-yl radical disubstituted in the 4-position with a phenyl or benzyl group and with a $(C_1-C_4)$alkyl, $(C_1-C_4)$alkoxy, cyano, aminocarbonyl, $(C_1-C_4)$alkyl-aminocarbonyl, di$(C_1-C_4)$alkylaminocarbonyl, $(C_1-C_3)$alkanoyl or $(C_1-C_3)$alkanoylamino group; the phenyl or benzyl groups substituting the piperidin-1-yl radical being unsubstituted or substituted with a halogen atom and/or a methyl and/or trifluoromethyl group;
$R_3$, $R_4$, $R_5$, $R_6$, $R_7$ and $R_8$ each represent, independently of one another, a hydrogen or halogen atom, or a $(C_1-C_6)$alkyl, $(C_1-C_6)$alkoxy or trifluoromethyl group;
$R_9$ represents a hydrogen atom, a $(C_1-C_4)$alkyl or cyano group or a $CH_2OH$, $CH_2CN$, or $CH_2O(C_1-C_4)$alkyl group;
$R_{10}$ and $R_{11}$, together with the nitrogen atom to which they are attached, constitute a saturated or unsaturated heterocyclic radical containing from 7 to 10 atoms, possibly containing a second hetero atom chosen from O and N, the said radical being unsubstituted or substituted one or more times with a $(C_1-C_4)$alkyl, hydroxyl, $(C_1-C_4)$alkoxy or methoxy$(C_1-C_2)$alkylene group, or substituted with a spirocyclobutane, a spirocyclopentane or a spirocyclohexane;
or $R_{10}$ and $R_{11}$, together with the nitrogen atom to which they are attached, constitute a saturated or unsaturated heterocyclic radical containing 5 or 6 atoms, containing a second nitrogen atom, the said radical being substituted one or more times with a methoxy$(C_1-C_2)$alkylene group, or substituted with a spirocyclobutane, a spirocyclopentane or a spirocyclohexane;
or $R_{10}$ and $R_{11}$, together with the nitrogen atom to which they are attached, constitute a saturated or unsaturated heterocyclic radical containing 5 or 6 atoms, possibly containing an oxygen atom, the said radical being substituted one or more times with a $(C_1-C_4)$alkyl, hydroxyl, $(C_1-C_4)$alkoxy or methoxy$(C_1-C_2)$alkylene group, or substituted with a spirocyclobutane, a spirocyclopentane or a spirocyclohexane;

and also the salts, the solvates and the hydrates thereof.

DETAILED DESCRIPTION OF THE INVENTION

The compounds of formula (I) may comprise one or more asymmetric carbon atoms. They may therefore exist in the form of enantiomers or of diastereoisomers. These enantiomers and diastereoisomers, and also the mixtures thereof, including the racemic mixtures, are part of the invention.

The compounds of formula (I) may exist in the form of bases or of addition salts with acids. These salts are advantageously prepared with pharmaceutically acceptable salts, but the salts of other acids that are useful, for example, for purifying or isolating the compounds of formula (I) are also part of the invention.

Among the compounds of formula (I), the compounds are distinguished in which:
$R_1$ represents hydrogen or a $(C_1-C_4)$alkyl;
$R_2$ represents:
  a saturated mononitrogenous heterocyclic radical containing from 5 to 7 atoms, the nitrogen atom being substituted with a $(C_1-C_4)$alkanoyl group;
  a group $NR_{10}R_{11}$;
  a nonaromatic $C_{11}-C_{12}$ carbocyclic radical which is unsubstituted or substituted one or more times with a $(C_1-C_4)$alkyl group;

a saturated monooxygenated heterocyclic radical containing from 5 to 7 atoms, which is substituted more than 3 times with a ($C_1$-$C_4$)alkyl group;

or $R_1$ and $R_2$, together with the nitrogen atom to which they are attached, constitute a piperidin-1-yl radical disubstituted in the 4-position with a phenyl or benzyl group and with a ($C_1$-$C_4$)alkyl or ($C_1$-$C_3$)alkanoyl group; the phenyl or benzyl groups substituting the piperidin-1-yl radical being unsubstituted or substituted with a halogen atom and/or a methyl group;

$R_3$, $R_4$, $R_5$, $R_6$, $R_7$ and $R_8$ each represent, independently of one another, a hydrogen or halogen atom, or a ($C_1$-$C_6$)alkyl, ($C_1$-$C_6$)alkoxy or trifluoromethyl group;

$R_9$ represents a hydrogen atom, a ($C_1$-$C_4$)alkyl or cyano group or a $CH_2OH$ or $CH_2O(C_1$-$C_4)$alkyl group;

$R_{10}$ and $R_{11}$, together with the nitrogen atom to which they are attached, constitute a saturated or unsaturated heterocyclic radical containing from 7 to 10 atoms, possibly containing a second hetero atom chosen from O and N, the said radical being unsubstituted or substituted one or more times with a ($C_1$-$C_4$)alkyl, hydroxyl, ($C_1$-$C_4$)alkoxy or methoxy($C_1$-$C_2$)alkylene group, or substituted with a spirocyclobutane, a spirocyclopentane or a spirocyclohexane;

or $R_{10}$ and $R_{11}$, together with the nitrogen atom to which they are attached, constitute a saturated or unsaturated heterocyclic radical containing 5 or 6 atoms, containing a second nitrogen atom, the said radical being substituted one or more times with a methoxy($C_1$-$C_2$)alkylene group, or substituted with a spirocyclobutane, a spirocyclopentane or a spirocyclohexane;

or $R_{10}$ and $R_{11}$, together with the nitrogen atom to which they are attached, constitute a saturated or unsaturated heterocyclic radical containing 5 or 6 atoms, possibly containing an oxygen atom, the said radical being substituted one or more times with a ($C_1$-$C_4$)alkyl, hydroxyl, ($C_1$-$C_4$)alkoxy or methoxy($C_1$-$C_2$)alkylene group, or substituted with a spirocyclobutane, a spirocyclopentane or a spirocyclohexane;

and also the salts, the solvates and the hydrates thereof.

The term "alkyl" is intended to mean a linear or branched radical such as, in particular: methyl, ethyl, propyl, isopropyl, butyl, isobutyl, tert-butyl, n-pentyl, isopentyl, n-hexyl or isohexyl, the methyl group being preferred for a ($C_1$-$C_4$) alkyl, the tert-butyl, 2-methyl-2-butyl and 3,3-dimethyl-2-butyl groups being preferred for a ($C_3$-$C_7$)alkyl.

The term "alkoxy" group is intended to mean a linear or branched radical, the methoxy group being preferred.

The term "halogen atom" is intended to mean a fluorine, chlorine, bromine or iodine atom; the fluorine, chlorine or bromine atom being preferred.

The nonaromatic $C_3$-$C_{12}$ carbocyclic radicals comprise monocyclic or polycyclic radicals that are fused or bridged. The monocyclic radicals include cycloalkyls, for example cyclopropyl, cyclobutyl, cyclopentyl, cyclohexyl, cycloheptyl and cyclooctyl; cyclohexyl and cyclopentyl being preferred. The di- or tricyclic radicals that are condensed, bridged or spiro radicals include, for example, norbornyl, bornyl, isobornyl, noradamantyl, adamantyl, spiro[5.5]undecanyl and bicyclo[2.2.1]heptanyl radicals; adamantyl being preferred.

The expression "saturated or unsaturated heterocyclic radical containing from 5 to 10 atoms, possibly containing a second hetero atom such as O or N" is intended to mean radicals such as morpholin-4-yl, piperidin-1-yl, piperazin-1-yl, pyrrolidin-1-yl, 3,6-dihydropyridin-1-yl or octahydrocyclopenta[c]-pyrrol-2-yl, the piperidin-1-yl and morpholin-4-yl radicals being preferred.

The expression "saturated mononitrogenous hetero-cyclic radical containing from 5 to 7 atoms" is intended to mean a radical such as piperidin-4-yl or pyrrolidin-3-yl, the piperadin-4-yl radical being preferred.

The expression "saturated monooxygenated hetero-cyclic radical containing from 5 to 7 atoms" is intended to mean a radical such as tetrahydrofuranyl, tetrahydro-2H-pyranyl or oxepanyl; tetrahydrofuranyl being preferred.

According to the present invention, preference is given to the compounds of formula (I) in which:
$R_1$ represents hydrogen;
$R_2$ represents: a group $NR_{10}R_{11}$; or
a nonaromatic $C_{11}$-$C_{12}$ carbocyclic radical which is unsubstituted or substituted one or more times with a methyl group;

or $R_1$ and $R_2$, together with the nitrogen atom to which they are attached, constitute a piperidin-1-yl radical disubstituted in the 4-position with a phenyl or benzyl group and with a ($C_1$-$C_4$)alkyl or ($C_1$-$C_3$)alkanoyl group;

and/or $R_3$, $R_4$, $R_5$, $R_6$, $R_7$ and $R_8$ each represent, independently of one another, a hydrogen or halogen atom, or a ($C_1$-$C_6$)alkyl, ($C_1$-$C_6$)alkoxy or trifluoromethyl group;

and/or $R_9$ represents a hydrogen atom or a methyl, methoxymethylene or cyano group;

$R_{10}$ and $R_{11}$, together with the nitrogen atom to which they are attached, constitute a saturated or unsaturated heterocyclic radical containing from 5 to 10 atoms, possibly containing an oxygen atom, the said radical being unsubstituted or substituted one or more times with a methyl group;

and also the salts, the solvates and the hydrates thereof.

Among the compounds which are the subject of the invention, mention may be made of the preferred compounds, which are defined by the following values for the substituents:

$R_1$ represents a hydrogen atom;
and $R_2$ represents the 3-amino-2,2,5,5-tetramethyl-tetrahydrofuran group;
or $R_1$ and $R_2$, together with the nitrogen atom to which they are attached, represent a 4-acetyl-4-phenylpiperidin-1-yl group;
and/or at least one of the substituents $R_3$, $R_4$ and $R_5$ represents a halogen atom, preferably chlorine or bromine, or a methoxy group;
and/or at least one of the substituents $R_6$, $R_7$ and $R_8$ represents a halogen atom, preferably chlorine or bromine;
and/or $R_9$ represents a methyl or methoxymethyl group.

Most particularly, the following compounds are preferred: 1-(1-(6-(4-chlorophenyl)-5-(2,4-dichlorophenyl)-2-methylpyridin-3-yl)-4-phenylpiperidin-4-yl)-ethanone, 6-(4-chlorophenyl)-5-(2,4-dichlorophenyl)-2-(methoxymethyl-N-(2,2,5,5-tetramethyltetrahydrofuran-3-yl)nicotinamide, 5-(4-chlorophenyl)-6-(2,4-dichlorophenyl)-2-methyl-N-(2,2,5,5-tetramethyltetrahydrofuran-3-yl) pyridine-3-carboxamide, 1-(1-(5-(4-bromophenyl)-6-(2,4-dichlorophenyl)-2-(methylpyridin-3-yl)carbonyl)-4-phenylpiperidin-4-yl) ethanone, and 6-(4-bromophenyl)-5-(2,4-dichlorophenyl)-2-methyl-N-(2,2,5,5-tetramethyl-tetrahydrofuran-3-yl) nicotinamide).

A subject of the present invention is also a process for preparing the compounds according to the invention.

This process is characterized in that a functional derivative of 5,6-diphenyl-2-pyridinecarboxylic acid, of formula:

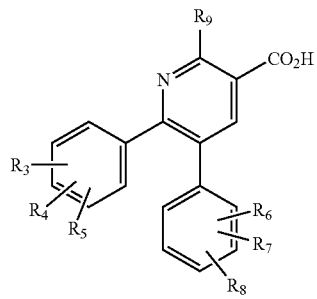

in which $R_3$, $R_4$, $R_5$, $R_6$, $R_7$, $R_8$ and $R_9$ are as defined for (I), is treated with an amine of formula $HNR_1R_2$ (III) in which $R_1$ and $R_2$ are as defined for (I). The compound thus obtained is optionally converted into one of its salts or solvates.

As functional derivative of the acid (II), use may be made of the acid chloride, the anhydride, a mixed anhydride, a $C_1$-$C_4$ alkyl ester in which the alkyl is linear or branched, an activated ester, for example the p-nitrophenyl ester, or the free acid activated at the right time, for example with N,N-dicyclohexylcarbodiimide or with benzotriazol-1-yloxotris(dimethylamino)-phosphonium hexafluorophosphate (BOP) or benzotriazol-1-yloxotris(pyrrolidino)phosphonium hexafluorophosphate (PyBOP).

Thus, in the process according to the invention, pyrazole-3-carboxylic acid chloride, obtained by reacting thionyl chloride with the acid of formula (II), can be reacted with an amine $HNR_1R_2$, in an inert solvent, such as a chlorinated solvent (dichloromethane, dichloroethane, chloroform, for example), an ether (tetrahydrofuran, dioxane, for example) or an amide (N,N-dimethylformamide, for example), under an inert atmosphere, at a temperature of between 0° C. and temperature, in the presence of a tertiary amine such as triethylamine, N-methylmorpholine or pyridine.

A variant consists in preparing the mixed anhydride of the acid of formula (II) by reacting ethyl chloroformate with the acid of formula (II), in the presence of a base such as triethylamine, and in reacting it with an amine $HNR_1R_2$, in a solvent such as dichloromethane, under an inert atmosphere, at ambient temperature, in the presence of a base such as triethylamine.

The compounds of formula (II) can be prepared by various processes, depending upon the nature of the substituent $R_9$.

For instance, Scheme 1 illustrates a mode for preparing the compounds of formula (II) in which $R_9$=($C_1$-$C_4$)alkyl, more specifically $R_9$=Me.

Step a1) is carried out in an anhydrous solvent such as THF; it is initiated at low temperature (−78° C.) and the temperature is then allowed to return to ambient temperature (AT).

Step b1) is carried out in the presence of acetic anhydride, at a temperature of between AT and 100° C.

Step c1) is carried out in an alcoholic solvent such as n-butanol, heating at the reflux of the solvent for 6 hours in the presence of a catalyst such as para-toluenesulfonic acid.

In step d1), the ester is hydrolyzed by heating in aqueous basic medium, in a solvent such as ethanol.

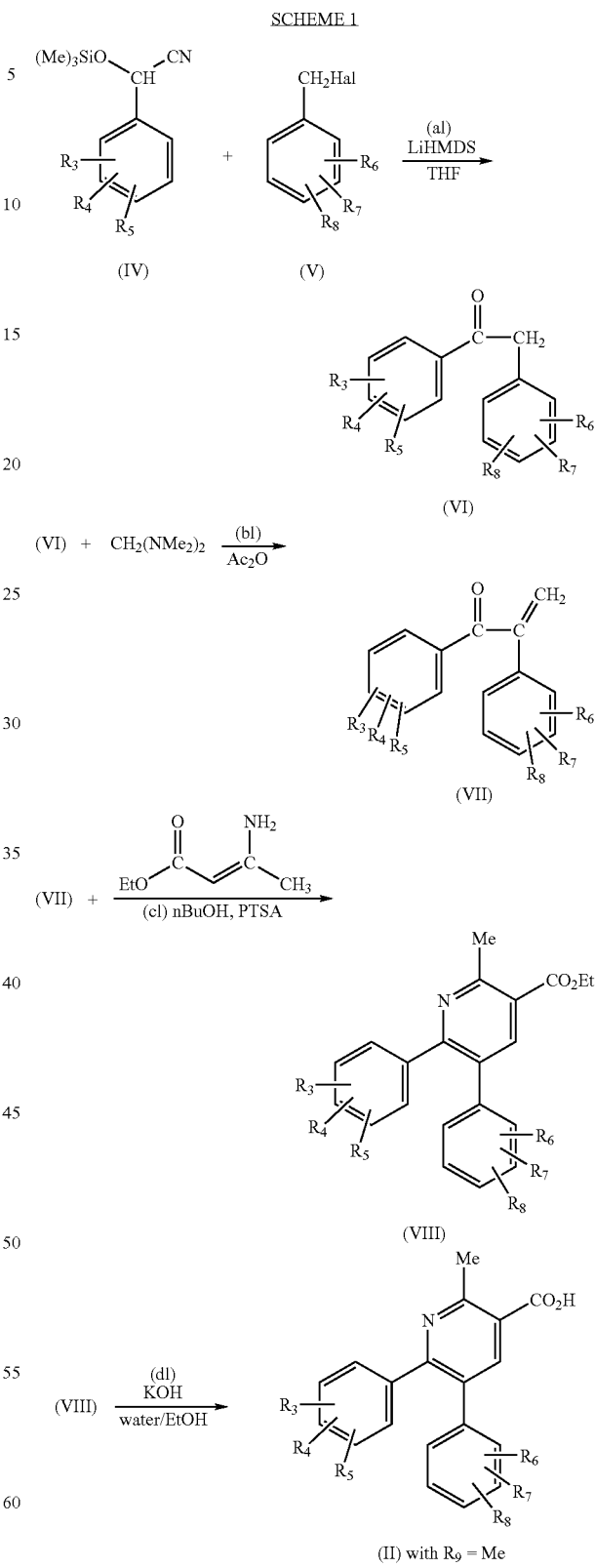

THF: tetrahydrofuran
LiHMDS: lithium hexamethyldisilazide
PTSA: para-toluenesulfonic acid.

SCHEME 2

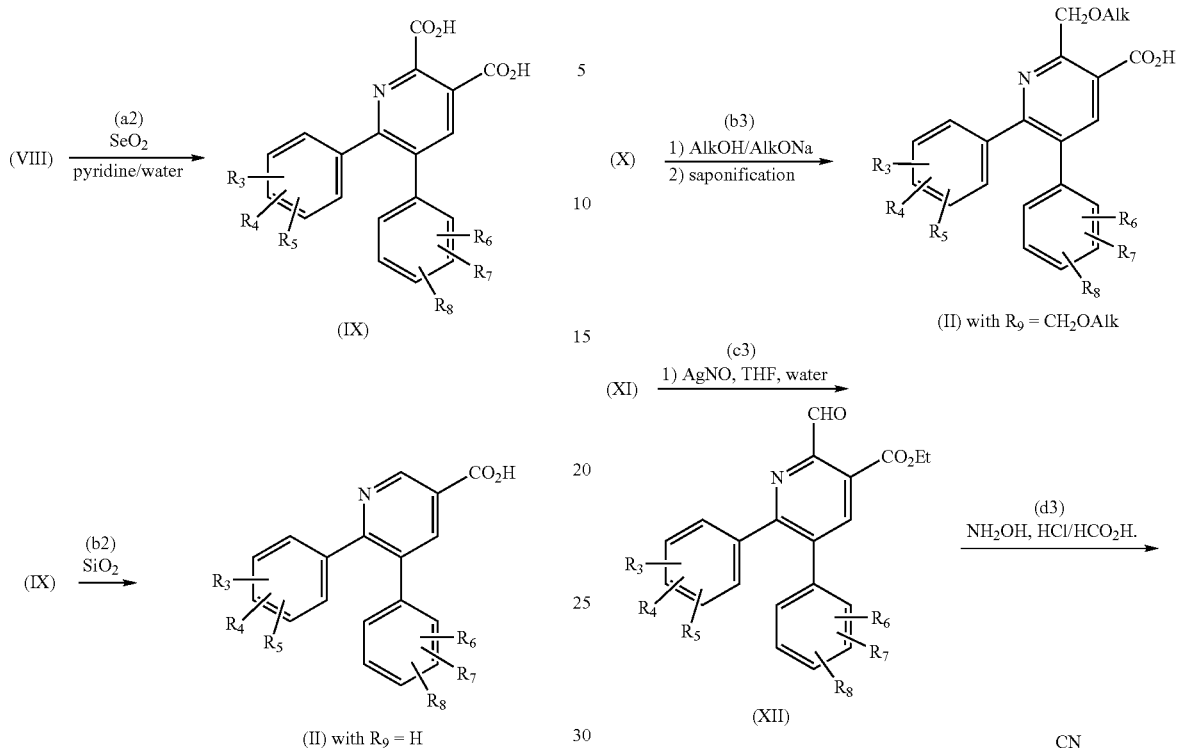

To prepare a compound of formula (II) in which $R_9$ is a hydrogen atom, the ester of formula (VIII) is treated with an oxidizing agent such as selenium oxide in pyridine in aqueous medium, and the diacid formed is then treated with silica under hot conditions, as illustrated in Scheme 2.

SCHEME 3

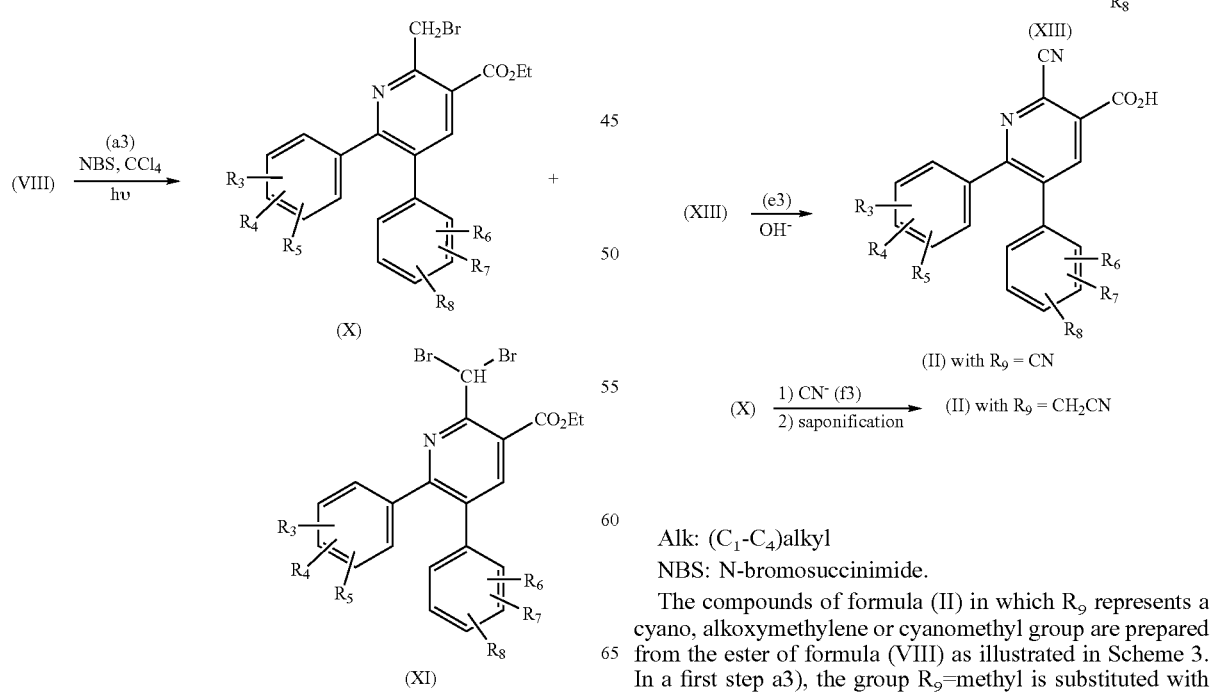

Alk: $(C_1-C_4)$alkyl

NBS: N-bromosuccinimide.

The compounds of formula (II) in which $R_9$ represents a cyano, alkoxymethylene or cyanomethyl group are prepared from the ester of formula (VIII) as illustrated in Scheme 3. In a first step a3), the group $R_9$=methyl is substituted with 1 or 2 bromine atoms by means of the action of N-bromosuccinimide, under hot conditions, in a solvent such as CCl$_4$, in the presence of UV radiation, so as to give a monobrominated derivative (X) and a dibrominated derivative (XI).

In step e3), the monobrominated derivative (X) is treated with a sodium alkoxide in an alcohol, for example sodium methoxide in methanol, and then saponified in basic medium, under hot conditions, to give the acid of formula (II) in which R$_9$ is the alkoxymethylene group.

In step f3), the monobrominated derivative (X) is treated with tetramethylammonium cyanide in a solvent such as chloroform, and then saponified under mild conditions, for example with LiOH in a THF/water mixture, to give the acid of formula (II) in which R$_9$ is the cyanomethyl group.

The dibrominated derivative (XI) is treated with silver nitrate in aqueous THF so as to form the aldehyde (XII), which is then treated with hydroxylamine hydrochloride in formic acid to give a nitrile derivative (XIII). The ester (XIII) is treated in basic medium, under mild conditions, preferably with LiOH, to give the acid of formula (II) in which R$_9$ is the cyano group.

To prepare a compound of formula (II) in which R$_9$=CH$_2$OH, the monobrominated derivative (X) is treated with sodium hydroxide, in a THF/water mixture, by refluxing, according to the following scheme.

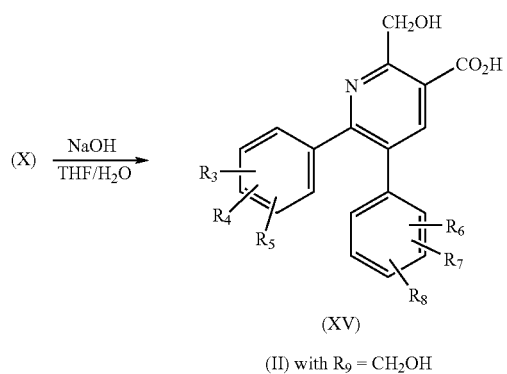

A compound of formula (II) in which R$_3$=CH$_2$OCH$_3$ can also be prepared by the method described in scheme 1 using an appropriate reagent in step c1, according to the following scheme:

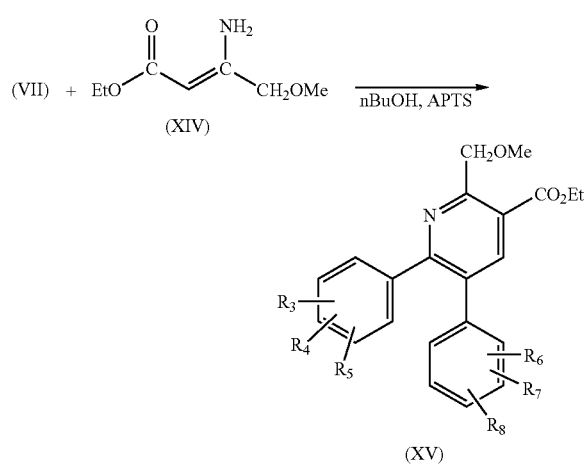

The reagent (XIV) is obtained according to the following reaction scheme:

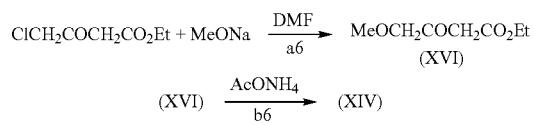

5, 6-Diphenyl-3-pyridinecarboxylic acids are generally known; 6-(4-chlorophenyl)-5-(4-methoxy-phenyl)-2-methylpyridine-3-carboxylic acid and 5,6-bis-(4-methoxyphenyl)pyridine-3-carboxylic acid and their ethyl esters are described in international patent application WO 2002/055502.

The amines HNR$_1$R$_2$ are known or are prepared by known methods such as those described in Chem. Ber., 1986, 119, 1413-1423.

The following abbreviations will be used in the present description:
DCM: dichloromethane
LDA: lithium diisopropylamide
THF: tetrahydrofuran
TFA: trifluoroacetic acid
AIBN: azobis(isobutyronitrile)
TMSiCl: trimethylchlorosilane
Et$_2$O or ether: ethyl ether
EtOAc: ethyl acetate
Ac$_2$O: acetic anhydride
nBuOH: n-butanol
PTSA: para-toluenesulfonic acid
LiHMDS: lithium hexamethyldisilazide
KHSO$_4$/K$_2$SO$_4$: 0.5 mol KHSO$_4$/0.19 mol K$_2$SO$_4$ in 1 liter of water
TEA: triethylamine
BOP: benzotriazol-1-yloxotris(dimethylamino) phosphonium hexafluorophosphate
PyBOP: benzotriazol-1-yloxotris(pyrrolidino) phosphonium hexafluorophosphate
NBS: N-bromosuccinimide
AT: ambient temperature
Mp: melting point.

The compounds according to the invention are analyzed by LC/UV/MS coupling (liquid chromatography/UV detection/mass spectrometry). The molecular peak (M$^+$) and the retention time (t) in minutes are measured.

A Symmetry C18 column, sold by Waters, of 2.1×50 mm, 3.5 μm, is used at ambient temperature, with a flow rate of 0.4 ml/minute.

The eluent has the following composition:
solvent A: 0.005% of trifluoroacetic acid (TFA) in water
solvent B: 0.005% of TFA in acetonitrile.

Gradient: The percentage of solvent B ranges from 0 to 90% over 10 minutes, with a plateau at 90% of B for 5 minutes.

The UV detection is carried out at 210 nm±8 nm and the detection of mass is carried out in positive ionization mode at atmospheric pressure.

The nuclear magnetic resonance (NMR) spectra are recorded at 200 MHz in d$_6$-DMSO. For analysis of the spectra, the following abbreviations are used: s: singlet; d: doublet; bs: broad singlet; dd: doublet of doublets; mt: multiplet.

Preparation 1

5-(2,4-Dichlorophenyl)-6-(4-chlorophenyl)-2-methyl-pyridine-3-carboxylic acid A) 1-(4-Chlorophenyl)-2-(2,4-dichlorophenyl)ethanone 32 g of LiHMDS are placed in 245 ml of THF at 0° C., and 40 g of (4-chlorophenyl) ((trimethylsilyl)oxy)acetonitrile are added slowly at −78° C., followed by 32.64 g of 2,4-dichloro-1-(chloromethyl)benzene. The temperature is allowed to return to AT overnight, and the reaction is then hydrolyzed with 170 ml of a 3N HCl solution, with gases being trapped in a solution of KOH (4N). After separation by settling out, the organic phase is evaporated, then taken up in DCM and agitated for 1 hour with 170 ml of NaOH (2N). The DCM is evaporated off and the expected compound is then crystallized from pentane. 38.6 g are obtained, Mp=119° C.

B) 1-(4-Chlorophenyl)-2-(2,4-dichlorophenyl)propen-2-en-1-one.

10 g of the compound from the preceding step, 17 ml of N,N,N-tetramethylmethanediamine and 17 ml of acetic anhydride are mixed at AT; the mixture is heated at 90° C. for 3 hours and is then allowed to return to AT. The mixture is poured into crushed ice and then filtered. The solid is dried under vacuum. 10 g of the expected compound are obtained, Mp=89° C.

C) 5-(2,4-Dichlorophenyl)-6-(4-chlorophenyl)-2-methylpyridine-3-carboxylic acid ethyl ester A mixture containing 7 g of the compound from the preceding step, 2.62 g of ethyl 3-amino-2-butenoate and 140 mg of para-toluenesulfonic acid is prepared in 60 ml of n-butanol and is then heated for 24 hours at the reflux of the solvent. Three quarters of the solvent is evaporated off and then 80 ml of pentane are added at 0° C. The precipitate formed is filtered off and the filtrate is concentrated. The residue is chromatographed on silica, elution being carried out with a cyclohexane/EtOAc (90/10; v/v) mixture. 7 g of the expected compound are obtained, Mp=114° C.

D) 5-(2,4-Dichlorophenyl)-6-(4-chlorophenyl)-2-methylpyridine-3-carboxylic acid 6 g of the ester obtained in the preceding step is placed in 300 ml of EtOH and 8 g of potassium hydroxide are added. After agitation for a few minutes, 5 ml of water are added and the mixture is refluxed for 19 hours. The reaction medium is concentrated and the product is taken up with $Et_2O$ and water. The aqueous phase is acidified to pH=1 with 10% HCl and is then extracted with DCM and dried over $Na_2SO_4$. After washing with heptane, 5.4 g of the expected compound are obtained.

NMR: 2.83 ppm: s: 3H; 7.2-7.6 ppm: unresolved peak: 5H, 7.68 ppm: s: 1H; 8.11 ppm: s: 1H; 13.2-13.7 ppm: bs: 1H.

Preparation 2

6-(4-Chlorophenyl)-5-(2,4-dichlorophenyl)pyridine-3-carboxylic acid

A) 6-(4-Chlorophenyl)-5-(2,4-dichlorophenyl)pyridine-2,3-dicarboxylic acid 2 g of the acid obtained in Preparation 1 are placed in 7.2 ml of pyridine and 0.8 ml of water and 1.44 g of selenium dioxide are added, and the mixture is then refluxed for 3 days. The solution obtained is filtered and then washed with acetic acid. After evaporation of the solvents, crushed ice is added and agitation is maintained for 2 hours. The solid formed is filtered off, washed with ether and then dried in an oven. The filtrate is concentrated and then filtered through silica, elution being carried out with DCM. The expected product is reacted as it is in the following step.

B) 6-(4-Chlorophenyl)-5-(2,4-dichlorophenyl)pyridine-3-carboxylic acid

The product obtained in the preceding step is solubilized in the minimum amount of DCM and impregnated onto 25 g of silica. After evaporation of the solvent, the silica is heated at 120° C. for 8 hours. The product formed is extracted with DCM+EtOH and then pure EtOH. After evaporation of the solvents, chromatography is performed on silica, elution being carried out with $CHCl_3$ and then $CHCl_3$/MeOH/AcOH (95/3/1.5; v/v/v). 544 mg of the expected compound are obtained.

NMR: 5.76 ppm: s: 1H; 7.2-7.6 ppm: unresolved peak: 5H; 7.69 ppm: s: 1H; 8.19 ppm: s: 1H; 9.22 ppm: s: 1H; 13.2-13.9 ppm: bs: 1H.

Preparation 3

6-(4-Chlorophenyl)-5-(2,4-dichlorophenyl)-2-methoxymethylpyridine-3-carboxylic acid A) 2-Bromomethyl-6-(4-chlorophenyl)-5-(2,4-dichlorophenyl)pyridine-3-carboxylic acid ethyl ester 3.8 g of ester obtained in Preparation 1, step C, are placed in 39 ml of $CCl_4$ with 7.07 g of NBS, and 10 mg of AIBN are added. The mixture is refluxed for 24 hours and then the heating is maintained for 8 hours with UV irradiation. After cooling, the reaction medium is filtered and the filtrate is chromatographed on silica, elution being carried out with DCM; 3.1 g of 2,2-dibromomethyl-6-(4-chlorophenyl)-5-(2,4-dichlorophenyl)pyridine-3-carboxylic acid ethyl ester and 1 g of 2-bromomethyl-6-(4-chlorophenyl)-5-(2,4-dichlorophenyl)pyridine-3-carboxylic acid ethyl ester are obtained.

B) 6-(4-Chlorophenyl)-5-(2,4-dichlorophenyl)-2-methoxymethylpyridine-3-carboxylic acid ethyl ester 1 g of the monobrominated compound obtained in the preceding step is placed in 30 ml of MeOH, and then 0.13 g of sodium methanolate is added and the mixture is refluxed for 24 hours. The reaction medium is hydrolyzed with a 10% HCl solution, and then the solvent is evaporated off and the product is taken up with EtOAc and washed with water. After drying over $MgSO_4$, the product is concentrated and then chromatographed on silica, elution being carried out with a cyclohexane/EtOAc (90/10; v/v) mixture. 840 mg of the expected ester are obtained.

C) 6-(4-Chlorophenyl)-5-(2,4-dichlorophenyl)-2-methoxymethylpyridine-3-carboxylic acid 800 mg of the ester obtained in the preceding step are placed in 37 ml of EtOH and 1.02 g of KOH are added, the mixture is then left at AT for 1 hour, with agitation, and 600 μl of water are added. The mixture is refluxed for 6 hours and the ethanol is then evaporated. The product is taken up with an Et$_2$O/water mixture and then separated by settling out. The aqueous phase is acidified at pH=2 by adding 1N HCl. 890 mg of the expected acid are obtained.

NMR: 3.36 ppm: s: 3H; 4.86 ppm: s: 2H; 7.2-7.4 ppm: unresolved peak: 4H; 7.48 ppm: s: 1H; 7.68: s: 1H; 8.08 ppm: s: 1H; 13.0-13.8: bs: 1H.

Preparation 3a

6-(4-Chlorophenyl)-5-(2,4-dichlorophenyl)-2-methoxymethylpyridine-3-carboxylic acid This compound can also be prepared according to the procedure described below.

A) Ethyl 4-methoxy-3-oxobutanoate 14 g of sodium hydride are introduced, under nitrogen, into 200 ml of DMF, the mixture is cooled to 0° C. and 6 ml of methanol in 100 ml of DMF are added dropwise and the mixture is left, with stirring, at 0° C. for 1 hour and then at AT for one hour. 17.32 g of 4-chloro-3-oxobutanoate in 100 ml of DMF are added, at 0° C., and the mixture is left overnight, with stirring. The reaction medium is poured into water at 0° C. and the mixture is then extracted with DCM, and washing is carried out 3 times with water and then 3 times with a saturated NaCl solution. The aqueous phase is taken up, acidified to pH>4, and then extracted with DCM, and washed 3 times with water and then with a saturated NaCl solution. The product is dried and then concentrated to dryness. The product is chromatographed on Celite®, elution being carried out with cyclohexane/EtOAc (80/20; v/v). 3.90 g of the expected compound are obtained in the form of a liquid.

B) Ethyl 3-amino-4-methoxybut-2-enoate

The molecular sieve (3 Å), 3.9 g of the compound obtained in the previous step and 4 g of freshly sublimated ammonium acetate, in 50 ml of cyclohexane, are placed under nitrogen and heated at 80° C. for 1 hour 30 minutes and then overnight at AT. The mixture is filtered and the filtrate is rinsed with CHCl$_3$. 2.4 g of the expected compound are obtained.

C) 6-(4-Chlorophenyl)-5-(2,4-dichlorophenyl)-2-methoxymethylpyridine-3-carboxylic acid ethyl ester 4.7 g of the compound of preparation 1, step B are dissolved in 25 ml of n-butanol by heating; 2.29 g of the compound obtained in the previous step in 5 ml of n-butanol are added, followed by 0.25 g of PTSA, and the mixture is refluxed for 19 hours. The reaction medium is triturated in Et$_2$O under cold conditions. Insoluble material is filtered off and the organic phase is concentrated and the product is then chromatographed on silica, elution being carried out with cyclohexane/EtOAc (95/5; v/v). 3.4 g of the expected compound are obtained.

G) 6-(4-Chlorophenyl)-5-(2,4-dichlorophenyl)-2-methoxymethylpyridine-3-carboxylic acid This compound is obtained as described in preparation 3, step C) above.

The intermediate compounds of formula (II) in the table below were also prepared according to the procedures described in the preparations above.

TABLE 1

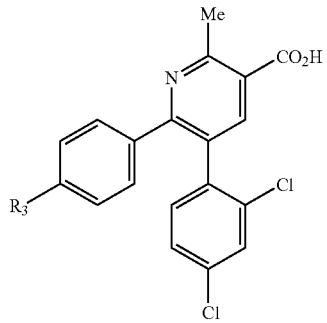

(II)

| Preparations | R$_3$ | Mp ° C. |
|---|---|---|
| 4 | OMe | 214° C. |
| 5 | Br | 214.5° C. |

EXAMPLE 1

Compound 3

1-(1-(6-(4-chlorophenyl)-5-(2,4-dichlorophenyl)-2-methylpyridin-3-yl)-4-phenylpiperidin-4-yl)ethanone 62.7 mg of the acid obtained in preparation 1 and 38.6 mg of 1-phenyl-1-piperidin-4-ylacetone are dissolved in 2 ml of DCM and 67.5 ml of triethylamine. 104 mg of PyBOP are subsequently added, and the reaction is left at AT for 2 hours, with stirring. After evaporation of the solvents, the crude is chromatographed on silica according to the following eluent gradient: pure dichloromethane then dichloromethane/methanol (99/1; v/v), 52 mg of the expected compound are obtained.

EXAMPLE 2

Compound 10

6-(4-chlorophenyl)-5-(2,4-dichlorophenyl)-2-(methoxy-methyl-N-(2,2,5,5-tetramethyltetrahydrofuran-3-yl)nicotinamide 0.42 g of the acid obtained in preparation 3 is placed in 2 ml of DCM and 0.34 g of (2,2,5,5-tetramethyltetrahydrofuran-3-yl)amine, 0.30 g of TEA and 0.60 g of PyBOP are added, and the mixture is left overnight, under nitrogen, with stirring. A solution of KHSO$_4$/K$_2$SO$_4$ is added, the mixture is stirred vigorously, and then extraction is carried out with DCM. The organic phase is washed with a saturated NaHCO$_3$ solution and then water. The product is dried and concentrated and the residue is then chromatographed on silica, elution being carried out with cyclohexane/EtOAc (3/1; v/v). 0.54 g of the expected compound is obtained. Mp=67-69° C.

The table below illustrates the chemical structures and the physical properties of some examples of compounds according to the invention.

In this table, Me, Et, nPr, tBu and nPn represent, respectively, methyl, ethyl, n-propyl, tert-butyl and n-pentyl groups.

TABLE 2

(I)

*Structure (I): a pyridine ring bearing R$_9$ at position 2 and C(O)–NR$_1$R$_2$ at position 3; position 6 substituted with a phenyl ring bearing R$_3$ and R$_4$; position 5 substituted with a phenyl ring bearing R$_6$ and R$_7$.*

| Compounds | R$_3$, R$_4$ | R$_6$, R$_7$ | R$_9$ | NR$_1$R$_2$ | Characterization |
|---|---|---|---|---|---|
| 1 | 4-Cl | 2,4-diCl | Me | —NH–(2,2,5,5-tetramethyltetrahydrofuran-3-yl) | M$^+$ = 517<br>t = 9.88 |
| 2 | 4-Cl | 2,4-diCl | Me | —NH–[(S)(-)-2-(methoxymethyl)pyrrolidin-1-yl] | M$^+$ = 504<br>t = 8.94 |
| 3 | 4-Cl | 2,4-diCl | Me | —N(4-acetyl-4-phenylpiperidin-1-yl) | M$^+$ = 577<br>t = 10.57 |
| 4 | 4-Cl | 2,4-diCl | Me | —NH–(2-azaspiro[5.5]... / 8-azaspiro[4.5]decan-8-yl) | M$^+$ = 528<br>t = 10.63 |
| 5 | 4-Cl | 2,4-diCl | Me | —NH–(4-ethyl-4-methylpiperidin-1-yl) | M$^+$ = 516<br>t = 10.47 |
| 6 | 4-OMe | 2,4-diCl | Me | —NH–(2,2,5,5-tetramethyltetrahydrofuran-3-yl) | Mp = 115.5° C. |
| 7 | 4-Br | 2,4-diCl | Me | —NH–(2,2,5,5-tetramethyltetrahydrofuran-3-yl) | Mp = 109.4° C. |

TABLE 2-continued (I)

| Compounds | R₃, R₄ | R₆, R₇ | R₉ | NR₁R₂ | Characterization |
|---|---|---|---|---|---|
| 8 | 2,4-diCl | 4-Br | Me | N-methylpiperidine with 4-phenyl and 4-C(O)Me | Mp = 210° C. |
| 9 | 4-Cl | 2,4-diCl | CH₂OMe | N-methylpiperidine with 4-phenyl and 4-C(O)Me | Mp = 102° C. |
| 10 | 4-Cl | 2,4-diCl | CH₂OMe | —NH- 2,2,5,5-tetramethyltetrahydrofuran-3-yl | Mp = 67° C. |
| 11 | 4-Br | 2,4-diCl | Me | N-methylpiperidine with 4-CN and 4-(4-Cl-phenyl) | Mp = 137° C. |
| 12 | 4-Br | 2,4-diCl | Me | N-methylpiperidine with 4-CN and 4-(3-CF₃-phenyl) | Mp = 128° C. |
| 13 | 4-Br | 2,4-diCl | Me | N-methylpiperidine with 4-OMe and 4-CH₂-phenyl | Mp = 110° C. |
| 14 | 4-Br | 2,4-diCl | Me | N-methylpiperidine with 4-CN and 4-(3-CF₃-phenyl) | Mp = 240° C. |
| 15 | 4-Br | 2,4-diCl | Me | N-methylpiperidine with 4-NH-COMe and 4-(4-F-phenyl) | Mp = 166° C. |

TABLE 2-continued

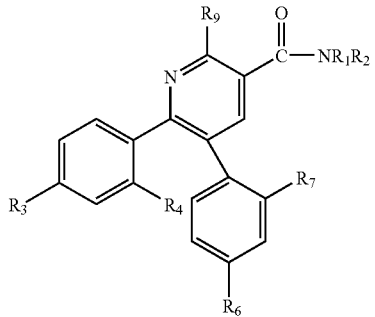

(I)

| Compounds | R₃, R₄ | R₆, R₇ | R₉ | NR₁R₂ | Characterization |
|---|---|---|---|---|---|
| 16 | 4-Cl | 2,4-diCl | Me | 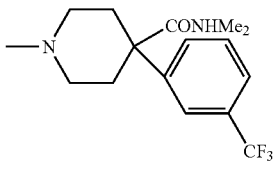 | Mp = 138° C. |
| 17 | 4-Cl | 2,4-diCl | Me | 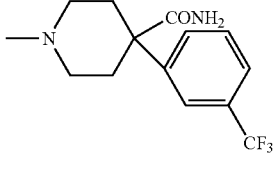 | Mp = 142° C. |
| 18 | 4-Cl | 2,4-diCl | Me | 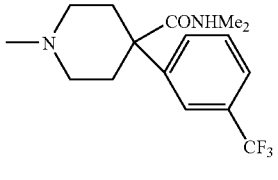 | Mp = 134° C. |
| 19 | 4-Br | 2,4-diCl | Me | 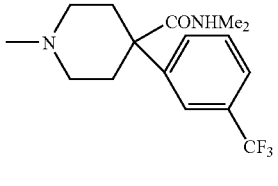 | M⁺ = 703<br>t = 10.57 |
| 20 | 4-Br | 2,4-diCl | Me | 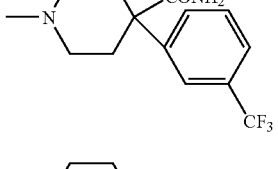 | M⁺ = 689<br>t = 11.05 |
| 21 | 4-Br | 2,4-diCl | Me | 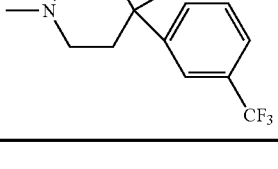 | M⁺ = 717<br>t = 11.96 |

The compounds according to the invention have been the subject of pharmacological trials for determining their cannabinoid $CB_1$ receptor antagonist effect.

The compounds of formula (I) possess a very good affinity in vitro ($IC_{50}$ between 5 nM and 1000 nM)) for cannabinoid $CB_1$ receptors, under the experimental conditions described by M. Rinaldi-Carmona et al. (FEBS Letters, 1994, 350, 240-244).

The antagonistic nature of the compounds of formula (I) was demonstrated by the results obtained in the adenylate cyclase inhibition models as described in M. Rinaldi-Carmona et al., J. Pharmacol. Exp. Therap., 1996, 278, 871-878 and M. Bouaboula et al., J. Biol. Chem., 1997, 272, 22330-22339.

The compounds according to the invention have been tested in vivo (ex vivo binding) in mice after the intravenous and/or oral administration of a compound of the invention, according to the experimental conditions described by Rinaldi-Carmona et al. (J. Pharmacol. Exp. Therap., 1998, 284, 644-650).

The toxicity of the compounds of formula (I) is compatible with their use as a medicinal product.

According to another of its aspects, the present invention relates to the use of a compound of formula (I), or of one of the pharmaceutically acceptable salts, solvates or hydrates thereof, for preparing medicinal products intended to treat or prevent diseases involving cannabinoid $CB_1$ receptors.

For example, and in a nonlimiting manner, the compounds of formula (I) are useful as psychotropic medicinal products, in particular for the treatment of psychiatric disorders, including anxiety, depression, mood disorders, insomnia, disorders involving delirium, obsessive disorders, psychoses in general, schizophrenia, attention deficit hyperactivity disorders (ADHD), in particular in hyperkinetic children (MBD), and also for the treatment of disorders related to the use of psychotropic substances, in particular in the case of substance abuse and/or substance addiction, including alcohol addiction and nicotine addiction.

The compounds of formula (I) according to the invention can be used as medicinal products for the treatment of migraine, stress, diseases of psychosomatic origin, panic attacks, epilepsy, locomotor disorders, in particular dyskinesias or Parkinson's disease, shaking and dystonia.

The compounds of formula (I) according to the invention can also be used as medicinal products in the treatment of memory disorders, cognitive disorders, in particular in the treatment of senile dementia and Alzheimer's disease, and also in the treatment of attention disorders or vigilance disorders. In addition, the compounds of formula (I) may be useful as neuroprotective agents, in the treatment of ischemia and cranial traumas and the treatment of neurodegenerative diseases: including chorea, Huntington's chorea and Tourette's syndrome.

The compounds of formula (I) according to the invention may be used as medicinal products in the treatment of pain: neuropathic pain, peripheral acute pain, chronic pain of inflammatory origin.

The compounds of formula (I) according to the invention may be useful as medicinal products in the treatment of appetite disorders, cravings (for sugars, carbohydrates, drugs, alcohols or any appetizing substance) and/or eating disorders, in particular as anorexigenic agents or for the treatment of obesity or bulimia, and also for the treatment of type II diabetes or non-insulin-dependent diabetes and for the treatment of dyslipidemia, metabolic syndrome. In addition, the compounds of formula (I) according to the invention may be used as medicinal products in the treatment of gastrointestinal disorders, diarrheic disorders, ulcers, vomiting, urinary and bladder disorders, disorders of endocrine origin, cardiovascular disorders, hypotension, hemorrhagic shock, septic shock, chronic liver cirrhosis, asthma, chronic bronchitis and chronic obstructive broncho-pneumopathy, Raynaud's syndrome, glaucoma, fertility disorders, inflammatory phenomena, immune system diseases, in particular autoimmune and neuroinflammatory diseases such as rheumatoid arthritis, reactional arthritis, diseases resulting in demyelinization, multiple sclerosis, infectious and viral diseases such as encephalitis, and cerebral strokes, and also as medicinal products for anticancer chemotherapy and for the treatment of Guillain-Barré syndrome.

According to the present invention, the compounds of formula (I) are most particularly useful for the treatment of psychotic disorders, in particular schizophrenia, attention deficit hyperactivity disorders (ADHD), in particular in hyperkinetic children (MBD); for the treatment of appetite disorders and obesity, for the treatment of memory and cognitive disorders; for the treatment of alcohol addiction or nicotine addiction, i.e. for alcohol withdrawal and tobacco withdrawal; for the treatment of dyslipidemia, metabolic syndrome.

According to one of its aspects, the present invention relates to the use of a compound of formula (I), of the pharmaceutically acceptable salts thereof and of the solvates or hydrates thereof, for the treatment of the disorders and diseases indicated above.

The compounds of formula (I) according to the invention can be used in combination with one or more other active principles that are useful for the prevention and/or treatment of the diseases indicated above: by way of example of active principles that may be combined with a compound of formula (I), mention may be made of antipsychotic agents, anxiolytics, agents for improving memory, anti-Parkinson agents, anti-epileptics, anorexigenic agents or other anti-obesity agents, nicotinic agonists, monoamine oxidase inhibitors, analgesics, anti-inflammatories, anti-hypertensives such as: $AT_1$ angiotensin II receptor antagonists, converting enzyme inhibitors, calcium antagonists, beta-blockers, anti-diabetic agents, blood lipid-lowering agents, blood cholesterol-lowering agents, PPAR (peroxisome proliferator activated receptor) agonists.

The compound according to the invention is generally administered as a dosage unit.

The said dosage units are preferably formulated in pharmaceutical compositions in which the active principle is mixed with a pharmaceutical excipient.

Thus, according to another of its aspects, the present invention relates to pharmaceutical compositions containing, as active principle, a compound of formula (I) or a pharmaceutically acceptable salt thereof, or a solvate thereof.

The compound of formula (I) above and the pharmaceutically acceptable salts or solvates thereof can be used at daily doses of 0.01 to 100 mg per kg of body weight of the mammal to be treated, preferably at daily doses of 0.02 to 50 mg/kg. In humans, the dose can preferably range from 0.05 to 4000 mg per day, more particularly from 0.1 to 1000 mg per day, depending on the age of the individual to be treated or the type of treatment, namely prophylactic or curative. Although these doses are examples of average situations, there may be particular cases where higher or lower doses are appropriate, such doses are also part of this invention. According to the usual practice, the dose which is suitable for each patient is determined by the physician according to the method of administration and the age, weight and response of the said patient.

In the pharmaceutical compositions of the present invention for oral, sublingual, inhaled, subcutaneous, intramuscular, intravenous, transdermal, local or rectal administration, the active principle can be administrated in unit administration form, as a mixture with conventional pharmaceutical supports, to animals and to humans. The suitable unit administration forms comprise oral-route forms such as tablets, gel capsules, powders, granules and oral solutions or suspensions, sublingual and buccal administration forms, aerosols, topical administration forms, implants, subcutaneous intramuscular, intravenous, intranasal or intraocular administration forms and rectal administration forms.

In the pharmaceutical compositions of the present invention, the active principle is generally formulated in dosage units containing from 0.05 to 1000 mg, advantageously from 0.1 to 500 mg, preferably from 1 to 200 mg, of the said active principle per dosage unit for daily administrations.

By way of example, a unit form of administration of a compound according to the invention in the form of a tablet may comprise the following components:

| | |
|---|---:|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

When taken orally, the dose of active principle administered per day can reach 0.01 to 100 mg/kg, taken in one or more doses, preferably 0.02 to 50 mg/kg.

There may be specific cases where higher or lower doses are appropriate; such dosages do not depart from the context of the invention. According to the usual practice, the dosage appropriate to each patient is determined by the physician according to the method of administration and the weight and the response of the said patient.

According to another of its aspects, the present invention also relates to a method of treating the pathologies indicated above, which comprises the administration, to a patient, of an effective dose of a compound according to the invention, or a pharmaceutically acceptable salt or hydrate or solvate thereof.

What is claimed is:

1. A compound of formula (I), including in the form of a base or an addition salt with an acid, or a hydrate or a solvate thereof:

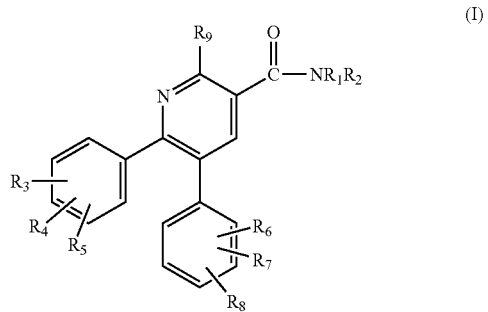

in which:
$R_1$ represents hydrogen or a $(C_1-C_4)$alkyl;
$R_2$ represents:
   a saturated mononitrogenous heterocyclic radical containing from 5 to 7 atoms, the nitrogen atom being substituted with an alkanoyl group;
   a group $NR_{10}R_{11}$;
   a nonaromatic $C_3-C_{10}$ carbocyclic radical which is substituted more than 3 times with a $(C_1-C_4)$alkyl group;
   a nonaromatic $C_{11}-C_{12}$ carbocyclic radical which is unsubstituted or substituted one or more times with a $(C_1-C_4)$alkyl group;
   a saturated monooxygenated heterocyclic radical containing from 5 to 7 atoms, which is substituted more than 3 times with a $(C_1-C_4)$alkyl group;

or $R_1$ and $R_2$, together with the nitrogen atom to which they are attached, constitute a piperidin-1-yl radical disubstituted in the 4-position with a phenyl or benzyl group and with a $(C_1-C_4)$alkyl, $(C_1-C_4)$alkoxy, cyano, aminocarbonyl, $(C_1-C_4)$alkylaminocarbonyl, di$(C_1-C_4)$alkylaminocarbonyl, $(C_1-C_3)$-alkanoyl or $(C_1-C_3)$alkanoylamino group; the phenyl or benzyl groups substituting the piperidin-1-yl radical being unsubstituted or substituted with a halogen atom and/or a methyl and/or trifluoromethyl group;

$R_3$, $R_4$, $R_5$, $R_6$, $R_7$ and $R_8$ each represent, independently of one another, a hydrogen or halogen atom, or a $(C_1-C_6)$alkyl, $(C_1-C_6)$alkoxy or trifluoromethyl group;

$R_9$ represents a hydrogen atom, a $(C_1-C_4)$alkyl or cyano group or a $CH_2OH$, $CH_2CN$ or $CH_2O(C_1-C_4)$alkyl group;

$R_{10}$ and $R_{11}$, together with the nitrogen atom to which they are attached, constitute a saturated or unsaturated heterocyclic radical containing from 7 to 10 atoms, possibly containing a second hetero atom chosen from O and N, the said radical being unsubstituted or substituted one or more times with a $(C_1-C_4)$alkyl, hydroxyl, $(C_1-C_4)$alkoxy or methoxy$(C_1-C_2)$alkylene group, or substituted with a spirocyclobutane, a spirocyclopentane or a spirocyclohexane;

or $R_{10}$ and $R_{11}$, together with the nitrogen atom to which they are attached, constitute a saturated or unsaturated heterocyclic radical containing 5 or 6 atoms, containing a second nitrogen atom, the said radical being substituted one or more times with a methoxy$(C_1-C_2)$alkylene group, or substituted with a spirocyclobutane, a spirocyclopentane or a spirocyclohexane;

or $R_{10}$ and $R_{11}$, together with the nitrogen atom to which they are attached, constitute a saturated or unsaturated heterocyclic radical containing 5 or 6 atoms, optionally containing an oxygen atom, the said radical being substituted one or more times with a $(C_1-C_4)$alkyl, hydroxyl, $(C_1-C_4)$alkoxy or methoxy$(C_1-C_2)$alkylene group, or substituted with a spirocyclobutane, a spirocyclopentane or a spirocyclohexane.

2. The compound of formula (I) as set forth in claim 1, wherein:
$R_1$ represents hydrogen;
$R_2$ represents:• a group $NR_{10}R_{11}$;
   a nonaromatic $C_{11}-C_{12}$ carbocyclic radical which is unsubstituted or substituted one or more times with a methyl group;
or $R_1$ and $R_2$, together with the nitrogen atom to which they are attached, constitute a piperidin-1-yl radical disubstituted in the 4-position with a phenyl or benzyl group and with a $(C_1-C_4)$alkyl or $(C_1-C_3)$alkanoyl group;
$R_3$, $R_4$, $R_5$, $R_6$, $R_7$ and $R_8$ each represent, independently of one another, a hydrogen or halogen atom, or a $(C_1-C_6)$alkyl, $(C_1-C_6)$alkoxy or trifluoromethyl group;
$R_9$ represents a hydrogen atom or a methyl, methoxymethylene or cyano group; and
$R_{10}$ and $R_{11}$, together with the nitrogen atom to which they are attached, constitute a saturated or unsaturated heterocyclic radical containing from 5 to 10 atoms, possibly containing an oxygen atom, the said radical being unsubstituted or substituted one or more times with a methyl group; and
said compound in the form of a base or an addition salt with an acid, or a hydrate or a solvate thereof.

3. The compound of formula (I) as set forth in claim 1, wherein:

R₁ represents a hydrogen atom;

R₂ represents 3-amino-2,2,5,5-tetramethyl-tetrahydrofuran group;

or R₁ and R₂, together with the nitrogen atom to which they are attached, represent a 4-acetyl-4-phenylpiperidin-1-yl group;

at least one of the substituents R₃, R₄ and R₅ represents a chlorine or bromine atom or a methoxy group;

at least one of the substituents R₆, R₇ and R₈ represents a chlorine or bromine atom;

and R₉ represents a methyl or methoxymethyl group; and said compound in the form of a base or an addition salt with an acid, or a hydrate or a solvate thereof.

4. The compound of formula (I) as set forth in claim 1, which is chosen from:

1-(1-(6-(4-chlorophenyl)-5-(2,4-dichlorophenyl)-2-methylpyridin-3-yl)-4-phenylpiperidin-4-yl)-ethanone, 6-(4-chlorophenyl)-5-(2,4-dichlorophenyl)-2-(methoxymethyl-N-(2,2,5,5-tetramethyl-tetrahydrofuran-3-yl)nicotinamide, 5-(4-chlorophenyl)-6-(2,4-dichlorophenyl)-2-methyl-N-(2,2,5,5-tetramethyltetrahydrofuran-3-yl)pyridine-3-carboxamide, 1-(1-(5-(4-bromophenyl)-6-(2,4-dichlorophenyl)-2-(methylpyridin-3-yl)carbonyl)-4-phenylpiperidin-4-yl) ethanone, and 6-(4-bromophenyl)-5-(2,4-dichlorophenyl)-2-methyl-N-(2,2,5,5-tetramethyltetrahydrofuran-3-yl)-nicotnamide, and said compound in the form of a base or an addition salt with an acid, or a hydrate or a solvate thereof.

5. A process for preparing a compound of formula (I) as set forth in claim 1, wherein a functional derivative of 5,6-diphenyl-3-pyridinecarboxylic acid, of formula:

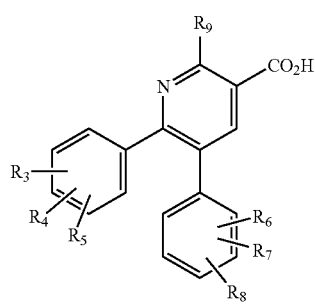

(II)

in which R₃, R₄, R₅, R₆, R₇, R₈ and R₉ are as defined for (I) in claim 1, is treated with an amine of formula HNR₁R₂ (III) in which R₁ and R₂ are as defined for (I) in claim 1.

6. A pharmaceutical composition comprising a compound of formula (I), including in the form of a base or an addition salt with an acid, or a hydrate or a solvate thereof, in combination with at least one pharmaceutically acceptable excipient:

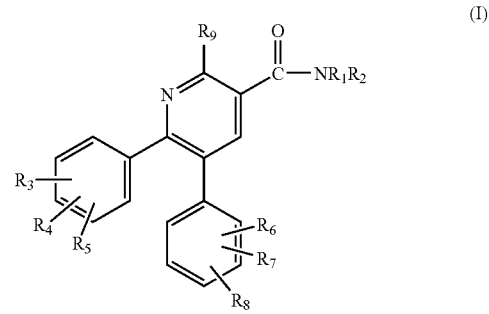

(I)

in which:

R₁ represents hydrogen or a ($C_1$-$C_4$)alkyl;

R₂ represents:

a saturated mononitrogenous heterocyclic radical containing from 5 to 7 atoms, the nitrogen atom being substituted with an alkanoyl group;

a group $NR_{10}R_{11}$;

a nonaromatic $C_3$-$C_{10}$ carbocyclic radical which is substituted more than 3 times with a ($C_1$-$C_4$)alkyl group;

a nonaromatic $C_{11}$-$C_{12}$ carbocyclic radical which is unsubstituted or substituted one or more times with a ($C_1$-$C_4$)alkyl group;

a saturated monooxygenated heterocyclic radical containing from 5 to 7 atoms, which is substituted more than 3 times with a ($C_1$-$C_4$)alkyl group;

or R₁ and R₂, together with the nitrogen atom to which they are attached, constitute a piperidin-1-yl radical disubstituted in the 4-position with a phenyl or benzyl group and with a ($C_1$-$C_4$)alkyl, ($C_1$-$C_4$)alkoxy, cyano, aminocarbonyl, ($C_1$-$C_4$)alkyl-aminocarbonyl, di($C_1$-$C_4$)alkylaminocarbonyl, ($C_1$-$C_3$)-alkanoyl or ($C_1$-$C_3$) alkanoylamino group; the phenyl or benzyl groups substituting the piperidin-1-yl radical being unsubstituted or substituted with a halogen atom and/or a methyl and/or trifluoromethyl group;

R₃, R₄, R₅, R₆, R₇ and R₈ each represent, independently of one another, a hydrogen or halogen atom, or a ($C_1$-$C_6$)alkyl, ($C_1$-$C_6$)alkoxy or trifluoromethyl group;

R₉ represents a hydrogen atom, a ($C_1$-$C_4$)alkyl or cyano group or a $CH_2OH$, $CH_2CN$ or $CH_2O$($C_1$-$C_4$)alkyl group;

R₁₀ and R₁₁, together with the nitrogen atom to which they are attached, constitute a saturated or unsaturated heterocyclic radical containing from 7 to 10 atoms, possibly containing a second hetero atom chosen from O and N, the said radical being unsubstituted or substituted one or more times with a ($C_1$-$C_4$)alkyl, hydroxyl, ($C_1$-$C_4$)alkoxy or methoxy($C_1$-$C_2$)alkylene group, or substituted with a spirocyclobutane, a spirocyclopentane or a spirocyclohexane;

or R₁₀ and R₁₁, together with the nitrogen atom to which they are attached, constitute a saturated or unsaturated heterocyclic radical containing 5 or 6 atoms, containing a second nitrogen atom, the said radical being substituted one or more times with a methoxy($C_1$-$C_2$)alkylene group, or substituted with a spirocyclobutane, a spirocyclopentane or a spirocyclohexane;

or R₁₀ and R₁₁, together with the nitrogen atom to which they are attached, constitute a saturated or unsaturated heterocyclic radical containing 5 or 6 atoms, optionally containing an oxygen atom, the said radical being substituted one or more times with a $(C_1-C_4)$alkyl, hydroxyl, $(C_1-C_4)$alkoxy or methoxy$(C_1-C_2)$alkylene group, or substituted with a spirocyclobutane, a spirocyclopentane or a spirocyclohexane.

7. The composition as set forth in claim 6, wherein:

$R_1$ represents hydrogen;

$R_2$ represents:• a group $NR_{10}R_{11}$;

a nonaromatic $C_{11}-C_{12}$ carbocyclic radical which is unsubstituted or substituted one or more times with a methyl group;

or $R_1$ and $R_2$, together with the nitrogen atom to which they are attached, constitute a piperidin-1-yl radical disubstituted in the 4-position with a phenyl or benzyl group and with a $(C_1-C_4)$alkyl or $(C_1-C_3)$alkanoyl group;

$R_3$, $R_4$, $R_5$, $R_6$, $R_7$ and $R_8$ each represent, independently of one another, a hydrogen or halogen atom, or a $(C_1-C_6)$alkyl, $(C_1-C_6)$alkoxy or trifluoromethyl group;

$R_9$ represents a hydrogen atom or a methyl, methoxymethylene or cyano group; and $R_{10}$ and $R_{11}$, together with the nitrogen atom to which they are attached, constitute a saturated or unsaturated heterocyclic radical containing from 5 to 10 atoms, possibly containing an oxygen atom, the said radical being unsubstituted or substituted one or more times with a methyl group.

8. The composition as set forth in claim 6, wherein:

$R_1$ represents a hydrogen atom;

$R_2$ represents 3-amino-2,2,5,5-tetramethyltetrahydrofuran group;

or $R_1$ and $R_2$, together with the nitrogen atom to which they are attached, represent a 4-acetyl-4-phenylpiperidin-1-yl group;

at least one of the substituents $R_3$, $R_4$ and $R_5$ represents a chlorine or bromine atom or a methoxy group;

at least one of the substituents $R_6$, $R_7$ and $R_8$ represents a chlorine or bromine atom;

and $R_9$ represents a methyl or methoxymethyl group.

9. The composition as set forth in claim 6, wherein the compound is chosen from:

1-(1-(6-(4-chlorophenyl)-5-(2,4-dichlorophenyl)-2-methylpyridin-3-yl)-4-phenylpiperidin-4-yl)-ethanone, 6-(4-chlorophenyl)-5-(2,4-dichlorophenyl)-2-(methoxymethyl-N-(2,2,5,5-tetramethyltetrahydrofuran-3-yl)nicotinamide, 5-(4-chlorophenyl)-6-(2,4-dichlorophenyl)-2-methyl-N-(2,2,5,5-tetramethyltetrahydrofuran-3-yl)pyridine-3-carboxamide, 1-(1-(5-(4-bromophenyl)-6-(2,4-dichlorophenyl)-2-(methylpyridin-3-yl)carbonyl)-4-phenylpiperidin-4-yl) ethanone, and 6-(4-bromophenyl)-5-(2,4-dichlorophenyl)-2-methyl-N-(2,2,5,5-tetramethyltetrahydrofuran-3-yl)-nicotinamide, and said compound in the form of a base or an addition salt with an acid, or a hydrate or a solvate thereof.

* * * * *